United States Patent [19]

Curtis et al.

[11] Patent Number: 4,565,570
[45] Date of Patent: Jan. 21, 1986

[54] ARYLACRYLARYL AMIDES HERBICIDAL COMPOUNDS AND METHODS OF USE

[75] Inventors: Jeff K. Curtis, Berkeley; William J. Michaely, Richmond, both of Calif.

[73] Assignee: Stauffer Chemical Company, Westport, Conn.

[21] Appl. No.: 710,195

[22] Filed: Mar. 11, 1985

Related U.S. Application Data

[63] Continuation-in-part of Ser. No. 560,367, Dec. 12, 1983, abandoned.

[51] Int. Cl.$^4$ .................... A01N 37/34; C07C 121/78
[52] U.S. Cl. ................................ 71/105; 260/465 D
[58] Field of Search .................... 260/465 D; 71/105

[56] References Cited

U.S. PATENT DOCUMENTS 3,726,662   4/1973   Howe et al. ...................... 71/105 X

OTHER PUBLICATIONS

Wolfbeis, Chem. Ber., 114(11), 3471–84 (1981).
Huppatz et al., Agric. Biol. Chem., 45(12), 2769–73 (1981).

*Primary Examiner*—Dolph H. Torrence
*Attorney, Agent, or Firm*—Michael J. Bradley

[57] ABSTRACT

A compound having the structural formula

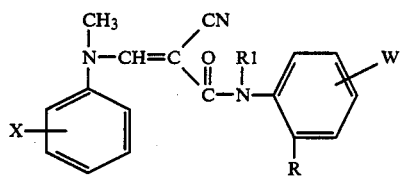

wherein R is halogen, including fluorine, chlorine, bromine and iodine, preferably chlorine, methyl, ethyl, ethenyl, ethinyl, carboxaldehyde, methoxy, nitro, trifluoromethyl or cyano, —S(O)$_n$CH$_3$, wherein n is 0, 1 or 2; —NH$_2$, —NHCH$_3$, —N(CH$_3$)$_2$, or —SO$_2$NH$_2$; provided that when R is hydrogen, W must be hydrogen and that when R is chlorine, W cannot be 4- or 6-chlorine; R$_1$ is hydrogen, C$_1$–C$_3$ alkyl or allyl; W is halogen, including fluorine, chlorine, bromine and iodine; trifluoromethyl, methyl, C$_1$–C$_3$ thioalkyl, —NHC(O)CH$_3$, or methoxy, provided that methoxy cannot be located in the 4-position on the ring; and X is in either the 2- or 3-position and can be halogen, including fluorine, chlorine, bromine, and iodine; thiomethyl, methyl or hydrogen.

35 Claims, No Drawings

ARYLACRYLARYL AMIDES HERBICIDAL COMPOUNDS AND METHODS OF USE

CROSS REFERENCE TO RELATED APPLICATIONS

This application is a continuation-in-part of application Ser. No. 560,367, filed Dec. 12, 1983, abandoned.

BACKGROUND OF THE INVENTION

The present invention relates to certain arylacrylaryl amide compounds which are useful as post-emergent herbicides against annual and perennial grasses and broadleaf weeds.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

Many arylacryl esters have been disclosed in the prior art [Huppatz, John L. et al., *Agric. Biol. Chem.*, 1982, 45(12), 2769–73 (Eng.)]. Several related arylacrylaryl amides have also been disclosed [Wolfbeis, Otto S., *Chem. Ber.*, 1981, 114(11), 3471–84] but no criticality of substitution patterns has been disclosed to result in highly active postemergent herbicides such as those disclosed and claims in this application.

Efforts are constantly being made, however, to find compounds which are equal to or greater in effectiveness than presently existing compounds, or which are more economical to produce.

DESCRIPTION OF THE INVENTION

This invention relates to the production of novel arylacrylaryl amide compounds and their use as herbicides. The novel compounds of this invention have the following structural formula

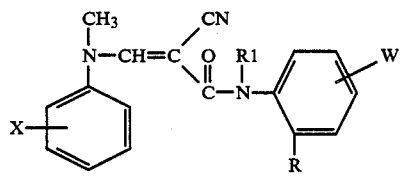

wherein

R is halogen, including fluorine, chlorine, bromine and iodine, preferably chlorine, methyl, ethyl, ethenyl, ethinyl, carboxaldehyde, methoxy, nitro, trifluoromethyl or cyano, —S(O)$_n$CH$_3$, wherein n is 0, 1 or 2; —NH$_2$, —NHCH$_3$, —N(CH$_3$)$_2$, or —SO$_2$NH$_2$; provided that when R is hydrogen, W must be hydrogen and that when R is chlorine, W cannot be 4- or 6-chlorine;

R$_1$ is hydrogen, C$_1$–C$_3$ alkyl or allyl;

W is halogen, including fluorine, chlorine, bromine and iodine; trifluoromethyl, methyl, C$_1$–C$_3$ thioalkyl, —NHC(O)CH$_3$, or methoxy, provided that methoxy cannot be located in the 4-position on the ring; and X is in either the 2- or 3-position and can be halogen, including fluorine, chlorine, bromine, and iodine; thiomethyl, methyl or hydrogen.

In the above description of the compounds of this invention, alkyl includes both straight and branched-chain configurations; including methyl, ethyl, n-propyl and isopropyl.

The compounds of the invention can be produced in a multi-step process in accordance with the following generalized sequence of steps. R, R$_1$, W and Y are as defined above.

REACTION NO. 1

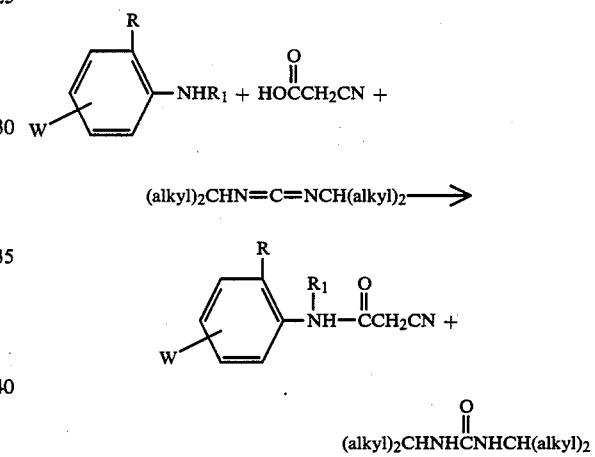

Generally, a 1.1 mole amount of a carbodiimide, dissolved in a one-to-one ratio of tetrahydrofuran and acetonitrile, is added to a mixture of one mole each of the substituted aniline and cyanoacetic acid in the same solvent system. The miture is stirred at room temperature for about 20 hours. Water (0.1 mole) is added and the mixture filtered. The product is dried over MgSO$_4$, filtered and evaporated.

REACTION NO. 2

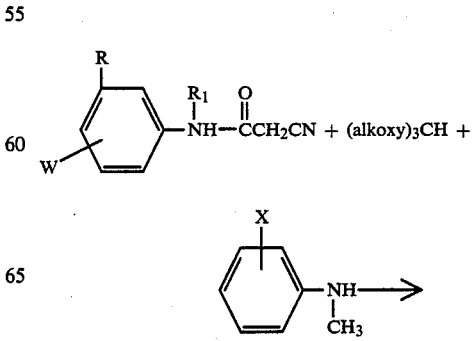

-continued

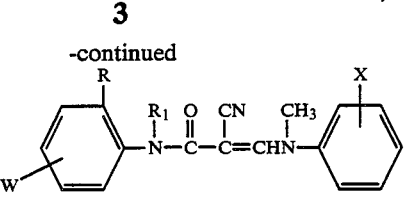

A mole amount each of an amine and the reaction product from Reaction No. 1 are combined with 3.5 moles of a trialkoxyorthocarboxylate. The mixture is heated for one hour while low boiling solvent is distilled off. The final product is purified by triturating in ethanol, filtering and air drying.

Examples 1 and 2 below illustrate methods of making the compounds of the invention using various starting materials. All intermediates and final products were identified by infrared, nuclear magnetic resonance and proton magnetic resonance spectrscopy.

EXAMPLE I

Preparation of N-(2-Nitrophenyl)-3-(N-methyl-N-phenyl)amino-2-cyanoacetamide

Step 1: 2-Nitroaniline (4.1 grams, 19 millimoles) was combined with 1.6 grams (g) (19 mmol) of cyanoacetic acid in 15 milliliters (ml) tetrahydrofuran (THF) and 15 ml $CH_3CN$. Diisopropylcarbodiimide (2.6 g, 21 mmol) dissolved in 3 ml THF was added dropwise. The reaction mixture exothermed and a white precipitate formed. The mixture was stirred at 20° C. for 20 hours, 5 ml water was added and the reaction mixture was stirred another 5 minutes. The precipitate was filtered off and the filtrate evaporated giving 6.6 g of a white solid which was then stirred in 100 ml $CH_3CN$, the insolubles filtered off and the filtrate evaporated to yield 5.1 g (18 mmol) of N-(2-nitrophenyl)-2-cyanoacetamide, a white solid (m.p. 151°–152° C.) (95% yield).

Step 2: Four grams of the product of Step 1 (19.5 mmol) was combined with 10 ml triethylorthoformate an 2.1 g (19.5 mmol) of N-methylaniline in a 50 ml flask fitted with a Vigreaux column and a distillation head. The mixture was heated with a mantle for one hour while distillate was collected between 55° and 79° C. Upon cooling the mixture solidified and was then slurried in 25 ml ethanol, filtered and the solid dried to yield 5.2 g (16 mmol) of the title compound, an orange solid having a melting point of 138°–141° C. The yield was 83%.

This compound will be referred to as Compound No. 3 throughout the remainder of the specification.

EXAMPLE 2

Preparation of N-(2-chlorophenyl)-3-methylphenylamino-2-cyanoacrylamide

Step 1: to a stirred solution of 25 g (200 mmol) o-chloroaniline in 500 ml methylene chloride. Twenty grams (9.9 mmol) of bromoacetyl bromide was added dropwise and then the reaction mixture was let stand for one hour. The solution was extracted two times with 1N HCl and the organic phase was reduced on the rota-vap.

The wet amide was dissolved in about 300 ml p-dioxane and 5.8 g (119 mmol) NaCN (sodium cyanide) and 80 ml water was added to it. The solution was slowly heated to reflux, then after two hours the solution was cooled and partially reduced on the rota-vap. $Et_2O$ was added to the residue and the organic layer was extracted with water, dryed over $MgSO_4$ and reduced on the rota-vap to yield 17.1 g (88 mmol) of N-(2-chlorophenyl)-2-cyanoacetamide.

Step 2: A mixture of 18.3 g of the cyanoamide product of Step 1, 13.3 g (89 mmol) of triethylorthoformate and 18.1 g (178 mmole) of acetic anhydride in a round-bottom flask was heated and reacted in an oil bath at 150° C. The ethyl acetate was collected by simple distillation. After one hour more of reaction more triethylorthoformate (3.3 g, 122 mmol) and acetic anhydride (4.5 g, 44 mmol) was added and heated as above.

A very dark solid was produced on cooling the reaction mixture. The solid was recrystallized in an ethanol/ether solvent to give 6.4 g (28 mmol) (29% yield) of a brown solid.

A portion of the brown solid (1.5 g, 6.7 mmol) and about 20 ml N-methylaniline in a round-bottom flask was heated on an oil bath at 150° C. for one hour. The solid was recrystallized with ethanol and further purified by column chromatography to yield 0.8 g (42% yield) of the title compound having a melting point of 110°–112° C.

This compound will be referred to as Compound No. 1 throughout the remainder of the specification.

The following is a table of certain selected compounds that are preparable according to the procedure described herein. Compound numbers are assigned to each compound and are used throughout the remainder of the application.

TABLE I

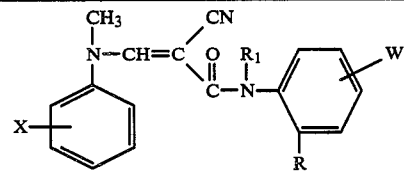

| Compound Number | R | $R_1$ | W | X | $n_D^{30}$ or melting point |
| --- | --- | --- | --- | --- | --- |
| 1 | —Cl | —H | —H | —H | 110–112 |
| 2 | —$OCH_3$ | —H | —H | —H | 120–122 |
| 3 | —$NO_2$ | —H | —H | —H | 138–141 |
| 4 | —I | —H | —H | —H | 107–109 |
| 5 | —$CH_3$ | —H | —H | —H | 135–136 |
| 6 | —CN | —H | —H | —H | 113–114 |
| 7 | —$CF_3$ | —H | —H | —H | 139–141 |
| 8 | —Br | —H | —H | —H | 108.5–110 |

TABLE I-continued

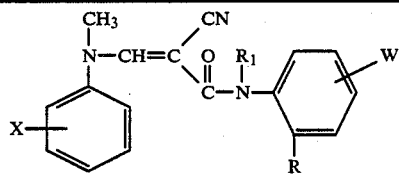

| Compound Number | R | $R_1$ | W | X | $n_D^{30}$ or melting point |
|---|---|---|---|---|---|
| 9 | —F | —H | —H | —H | 124–125 |
| 10 | —H | —CH₃ | —H | —H | 1.5716 |
| 11 | —Cl | —H | —H | 3-Cl | 94–96 |
| 12 | —H | —H | —H | —H | white solid |
| 13 | —Cl | —H | 5-Cl | —H | white solid |
| 14 | —NH₂ | —H | —H | —H | glass |
| 15 | —Cl | —CH₃ | —H | —H | glass |
| 16 | —Cl | —H | —CH₃ | —H | 131–133 |
| 17 | —CHO | —H | —H | —H | glass |
| 18 | —CH₂CH₃ | —H | —H | —H | 106–107 |
| 19 | —SCH₃ | —H | —H | —H | 125–127 |
| 20 | —F | —H | 6-F | —H | 194–196 |
| 21 | —F | —CH₃ | —H | 2-Cl | 153–155 |
| 22 | —Cl | —H | 5-CH₃ | —H | 121–124 |
| 23 | —CH₃ | —H | 4-Br | —H | 121–125 |
| 24 | —CF₃ | —H | 4-Cl | —H | 120–123 |
| 25 | —CH=CH₂ | —H | —H | —H | 124–125 |
| 26 | —Cl | —H | 5-CF₃ | —H | 123–124 |
| 27 | —Cl | —H | —CH₃ | 2-Cl | 142–143 |
| 28 | —SCH₃ | —H | —CH₃ | 2-Cl | 137–139 |
| 29 | —SCH₃ | —CH₃ | —H | 2-Cl | 104–106 |
| 30 | —Cl | —H | —OCH₃ | —H | 151–153 |
| 31 | —Cl | —CH₃ | —H | 2-Cl | 132–135 |
| 32 | —SO₂NH₂ | —H | —H | —H | 125–130 |
| 33 | —NH₂ | —H | —H | —H | 82–86 |
| 34 | —I | —CH₃ | —H | —H | 126–129 |
| 35 | —NO₂ | —H | 4-CH₃ | —H | 164–165 |
| 36 | —Cl | —CH₂CH₃ | —H | —H | viscous oil |
| 37 | —Cl | —CH₂CH=CH₂ | —H | —H | viscous oil |
| 38 | —SO₂CH₃ | —H | —H | —H | 146–148 |
| 39 | —Cl | —H | —SCH₂CH₃ | —H | 122–126 |
| 40 | —H | —CH₂CH=CH₂ | —H | —H | viscous oil |
| 41 | —Br | —H | 4-CF₃ | —H | 79–89 |
| 42 | —OCH₃ | —H | 5-OCH₃ | —H | 105–106 |
| 43 | —F | —H | 5-CF₃ | —H | 118–119 |
| 44 | —SOCH₃ | —H | —H | —H | viscous oil |
| 45 | —CN | —H | —H | —H | 104–106 |
| 46 | —Cl | —H | 5-NCOCH₃ | —H | 146–151 |

HERBICIDAL SCREENING TESTS

As previously mentioned, the herein described compounds produced in the above-described manner are phytotoxic compounds which are useful and valuable in controlling various plant species. Selected compounds of this invention were tested as herbicides in the following manner.

Post-emergence herbicide test

Seven grass and broadleaf weed species, including green foxtail (FT) (*Setaria viridis*), watergrass (WG) (*Echinochloa crus-galli*), wild oat (WO) (*Avena fatua*), annual morningglory (AMG) (*Ipomoea purpurea*), velvetleaf (VL) (*Abutilon theophrasti*), mustard (MD) (*Brassica kaber*) and curly dock (CD) (*Rumex crispus*), are seeded in individual rows in 6×10×3 inch flats. The flats are placed in the greenhouse, watered daily (both before and after chemical treatment) with a sprinkler and maintain at about 78° F. Chemical spray treatment is made 12 days after planting. The spray is prepared by weighing out 333 mg of compound and dissolving in 25 ml acetone containing 1% polyoxyethylene sorbitan monolaurate emulsifier. From this stock solution 18 ml are removed and brought up to a 40 ml volume with a 19:1 water/acetone mixture. The carrier volume is 80 gallons/A (748 L/ha) and a 4 lb/A (4.48 kg/ha) rate is used.

Watering of the treated flats is confined to the soil surface and not to the foliage of the sprouted plants. Twelve-fourteen Days after treatment, the degree of injury or control is determined by comparison with untreated check plants of the same age. The injury rating from 0 to 100% is recorded for each species as percent control with 0% representing no injury and 100% representing complete control.

The results of the post-emergence herbicide test are reported in Table II.

TABLE II

Post-Emergence Herbicidal Activity
Application Rate - 4.48 kg/ha

| Cmpd. No. | FT | WG | WO | AMG | VL | MD | CD | AVE GR | AVE BL |
|---|---|---|---|---|---|---|---|---|---|
| 1 | 95 | 80 | 60 | 100 | 100 | 100 | 40 | 78 | 85 |
| 2 | 100 | 60 | 30 | 100 | 100 | 100 | 90 | 63 | 98 |
| 3 | 60 | 40 | 10 | 20 | 40 | 60 | 0 | 37 | 30 |
| 4 | 100 | 60 | 60 | 100 | 100 | 100 | 80 | 73 | 95 |
| 5 | 90 | 100 | 100 | 100 | 100 | 100 | 0 | 97 | 75 |
| 6 | 100 | 100 | 100 | 60 | 100 | 100 | 40 | 100 | 75 |
| 7 | 90 | 20 | 10 | 60 | 80 | 90 | 20 | 40 | 63 |
| 8 | 100 | 80 | 50 | 80 | 100 | 100 | 20 | 77 | 70 |
| 9 | 100 | 90 | 80 | 100 | 100 | 100 | 100 | 90 | 100 |
| 10 | 40 | 40 | 20 | 20 | 40 | 40 | 0 | 33 | 25 |
| 11 | 90 | 60 | 40 | 80 | 100 | 100 | 0 | 63 | 70 |
| 12 | 60 | 40 | 20 | 90 | 100 | 100 | 60 | 40 | 88 |
| 13 | 60 | 40 | 10 | 60 | 60 | 60 | 20 | 37 | 50 |
| 14 | 80 | 20 | 0 | 80 | 100 | 100 | 20 | 33 | 75 |
| 15 | 100 | 90 | 60 | 100 | 80 | 90 | 100 | 83 | 93 |
| 16 | 90 | 65 | 40 | 85 | 100 | 100 | 0 | 65 | 71 |
| 17 | 90 | 100 | 40 | 80 | 90 | 90 | 80 | 77 | 85 |
| 18 | 90 | 60 | 40 | 80 | 90 | 90 | 40 | 63 | 75 |
| 19 | 60 | 20 | 10 | 40 | 60 | 40 | 20 | 30 | 40 |
| 20 | 40 | 20 | 0 | 40 | 20 | 20 | 40 | 20 | 30 |
| 21 | 100 | 70 | 80 | 65 | — | 100 | 40 | 83 | 68 |
| 22 | 100 | 70 | 20 | 85 | — | 100 | 60 | 63 | 82 |
| 23 | 100 | 60 | 100 | 60 | — | 90 | 65 | 87 | 72 |
| 24 | 100 | 70 | 100 | 85 | — | 85 | 75 | 90 | 82 |
| 25 | 40 | 40 | 15 | 90 | 70 | 35 | 45 | 32 | 60 |
| 26 | 100 | 90 | 90 | 45 | 80 | 100 | 95 | 93 | 80 |
| 27 | 90 | 90 | 30 | 40 | 60 | 90 | 90 | 70 | 70 |
| 28 | 45 | 60 | 0 | 25 | 0 | 15 | 0 | 35 | 10 |
| 29 | 20 | 10 | 15 | 65 | 70 | 70 | 50 | 15 | 64 |
| 30 | 100 | 25 | 45 | 25 | — | 100 | 60 | 57 | 62 |
| 31 | 0 | 20 | 40 | 65 | 100 | 80 | 80 | 20 | 81 |
| 32 | 100 | 0 | 20 | 40 | 100 | 100 | 60 | 40 | 75 |
| 33 | 70 | 0 | 0 | 100 | 100 | 100 | 0 | 23 | 75 |
| 34 | 0 | 0 | 0 | 90 | 100 | 100 | 100 | 0 | 98 |
| 35 | 0 | 0 | 0 | 20 | 40 | 70 | 0 | 0 | 33 |
| 36 | 20 | 0 | 0 | 80 | 90 | 100 | 15 | 7 | 71 |
| 37 | 0 | 0 | 0 | 80 | 0 | 100 | 0 | 0 | 45 |
| 38 | 0 | 0 | 0 | 0 | 0 | 100 | 0 | 0 | 25 |
| 39 | 80 | 0 | 0 | 15 | 70 | 100 | 0 | 27 | 46 |
| 40 | 100 | 20 | 0 | 30 | 100 | 100 | 100 | 40 | 80 |
| 41 | 50 | 20 | 0 | 0 | 50 | 90 | 70 | 30 | 53 |
| 42 | 25 | 0 | 0 | 25 | 20 | 100 | 60 | 8 | 51 |
| 43 | 0 | 0 | 20 | 100 | 100 | 100 | 100 | 7 | 100 |
| 44 | 60 | 20 | 40 | 100 | 100 | 100 | 20 | 40 | 80 |
| 45 | 100 | 15 | 20 | 100 | 100 | 100 | 0 | 45 | 75 |
| 46 | 0 | 0 | 15 | 10 | 20 | 30 | 10 | 8 | 18 |

AVE GR = The average of all grass weeds treated at the application rate.
AVE BL = The average of all broadleaf weeds treated at the application rate.

The compounds of the present invention are useful as herbicides, especially as post-emergence herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for post-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the weeds either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil as a dispersion in water or other liquid. These granules are dust-free and free flowing when dry and yet upon dilution in water, form homogeneous dispersions. Typical carriers for dry flowables include fuller's earth, kaolin clays, silicas and other readily available wet organic or inorganic diluents. The dry flowables normally are prepared to contain 5% to about 95% of the active ingredient and usually contains a small amount of wetting, dispersing or emulsifying agent to facilitae wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

EXAMPLES OF TYPICAL FORMULATIONS

| Ingredient | Weight % |
| --- | --- |
| Oil | |
| Compound 1 | 1 |
| Oil solvent-heavy aromatic naphtha | 99 |
| Total | 100 |
| Emulsifiable Concentrate | |
| Compound 2 | 50 |
| Kerosene | 45 |
| Emulsifying agent (mixture of long chain ethoxylated polyethers with long chain sulfonate) | 5 |
| Total | 100 |
| Emulsifiable Concentrate | |
| Compound 3 | 90 |
| Kerosene | 5 |
| Emulsifying agent (mixture of long chain ethoxylated polyethers with long chain sulfonate) | 5 |
| Total | 100 |

Dusts and/or Powders

| Ingredient | Wt. % | Wt. % | Wt. % |
| --- | --- | --- | --- |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chloropenoxyacetic acid and the salts, esters and amides thereof, triazine derivatives, such as 2,4-bis(3-methoxypropylamino)-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1- dimethylurea; and acetamides such as N,N-diallyl-α-chloroacetamide, and the like; benzoic acids such as 3-amino-2,5-dichlorobenzoic acid; thiocarbmates such as S-propyl, N,N-dipropylthiocarbamate, S-ethyl N,N-dipropylthiocarbmate, S-ethyl cyclohexylethylthiocarbamate, S-ethyl hexahydro-1H-azepine-1-carbothioate and the like; anilines such as 4-(methylsulfonyl)-2,6-dinitro-N,N-substituted aniline, 4-trifluoromethyl-2,6-dinitro-N,N-di-n-propyl aniline, 4-trifluoromethyl-2,6-dinitro-N-ethyl-N-butyl aniline, 2-[4-(2,4-dichlorophenoxy)phenoxy]propanoic acid, 2-[1-(ethoxyimino)-butyl]-5-[2-ethylthio)propyl]-3-hydroxy-2-cyclohexene-1-one, (±)-butyl-2-[4-[(5-trifluoromethyl)-2-pyridinyl)oxy]-phenoxy]propanate, sodium 5-[2-chloro-4-(trifluoromethyl)phenoxy]-2-nitrobenzoate, 3-isopropyl-1H-2,1,3-benzothiadiazine-4(3H)-one-2,2-dioxide, and 4-amino-6-tert-butyl-3-(methylthio)-as-triazin-5(4H)-one or (4-amino-6-(1,1-dimethylethyl)-3-(methylthio)-1,2,4-triazin-5(4H)-one). Fertilizers useful in combination with the active ingredients include, for example, ammonium nitrate, urea and superphosphate. Other useful additaments include materials in which plant organisms take root and grow such as compost, manure, humus, sand, and the like.

We claim:
1. A compound having the structural formula

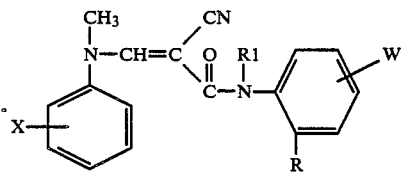

wherein
R is selected from the group consisting of fluorine, chlorine, bromine, iodine, methyl, ethyl, ethenyl, ethinyl, carboxaldehyde, methoxy, nitro, trifluoromethyl, cyano, —S(O)$_n$CH$_3$ where n is 0, 1 or 2; —NH$_2$, —NHCH$_3$, —N(CH$_3$)$_2$ and —SO$_2$NH$_2$, provided that when R is hydrogen, W must be hydrogen and that when R is chlorine, W cannot be 4- or 6-chlorine;

R$_1$ is selected from the group consisting of hydrogen, C$_1$–C$_3$ alkyl or allyl;

W is selected from the group consisting of fluorine, chlorine, bromine, iodine, trifluoromethyl, methyl, C$_1$–C$_3$ thioalkyl, —NHC(O)CH$_3$ and methoxy provided that methoxy is not 4-methoxy; and X is selected from the group consisting of 2- or 3-fluorine, chlorine, bromine, iodine, thiomethyl, methyl and hydrogen.

2. The compound of claim 1 wherein R is chlorine and R$_1$, W and X are hydrogen.
3. The compound of claim 1 wherein R is methoxy and R$_1$, W and X are hydrogen.
4. The compound of claim 1 wherein R is nitro and R$_1$, W and X are hydrogen.
5. The compound of claim 1 wherein R is iodine and R$_1$, W and X are hydrogen.
6. The compound of claim 1 wherein R is methyl and R$_1$, W and X are hydrogen.
7. The compound of claim 1 wherein R is cyano and R$_1$, W and X are hydrogen.
8. The compound of claim 1 wherein R is bromine and R$_1$, W and X are hydrogen.

9. The compound of claim 1 wherein R is fluorine and R$_1$, W and X are hydrogen.
10. The compound of claim 1 wherein R is trifluoromethyl and R$_1$, W and X are hydrogen.
11. The compound of claim 1 wherein R is chlorine, R$_1$ and W are hydrogen and X is 3-chlorine.
12. The compound of claim 1 wherein R, R$_1$, W and X are hydrogen.
13. The compound of claim 1 wherein R is —NH$_2$ and R$_1$, W and X are hydrogen.
14. The compound of claim 1 wherein R is chlorine, R$_1$ is methyl, W and X are hydrogen.
15. The compound of claim 1 wherein R is fluorine, R$_1$ is methyl, W is hydrogen and X is chlorine.
16. The compound of claim 1 wherein R is iodine, R$_1$ is methyl and W and X are hydrogen.
17. The compound of claim 1 wherein R is hydrogen, R$_1$ is allyl and W and X are hydrogen.
18. A herbicidal composition comprising an herbicidally effective amount of a compound having the srtructural formula

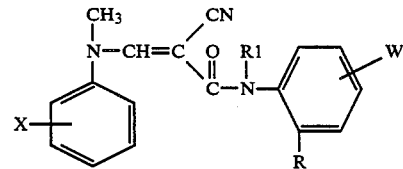

wherein
R is selected from the group consisting of fluorine, chlorine, bromine, iodine, methyl, ethyl, ethenyl, ethinyl, carboxaldehyde, methoxy, nitro, trifluoromethyl, cyano, —S(O)$_n$CH$_3$ wherein n is 0, 1 or 2; —NH$_2$, —NHCH$_3$, —N(CH$_3$)$_2$ and —SO$_2$NH$_2$, provided that when R is hydrogen, W must be hydrogen and that when R is chlorine, W cannot be 4- or 6-chlorine;

R$_1$ is selected from the group consisting of hydrogen, C$_1$–C$_3$ alkyl or allyl;

W is selected from the group consisting of fluorine, chlorine, bromine, iodine, trifluoromethyl, methyl, C$_1$–C$_3$ thioalkyl, —NHC(O)CH$_3$ and methoxy provided that methoxy is not 4-methoxy; and X is selected from the group consisting of a 2- or 3-fluorine, chlorine, bromine, iodine, thiomethyl, methyl and hydrogen; and an inert carrier.

19. The method of controlling undesirable vegetation comprising applying to the area where control is desired, an herbicidally effective amount of a compound having the formula

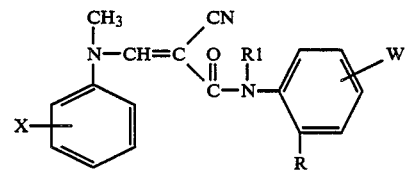

wherein
R is selected from the group consisting of fluorine, chlorine, bromine, iodine, methyl, ethyl, ethenyl, ethinyl, carboxaldehyde, methoxy, nitro, trifluoromethyl, cyano, —S(O)$_n$CH$_3$ where n is 0, 1 or 2; —NH$_2$, —NHCH$_3$, —N(CH$_3$)$_2$ and —SO$_2$NH$_2$, provided that when R is hydrogen, W must be hydrogen and that when R is chlorine, W cannot be 4- or 6-chlorine;

$R_1$ is selected from the group consisting of hydrogen, $C_1$-$C_3$ alkyl or allyl;

W is selected from the group consisting of fluorine, chlorine, bromine, iodine, trifluoromethyl, methyl, $C_1$-$C_3$ thioalkyl, —NHC(O)CH$_3$ and methoxy provided that methoxy is not 4-methoxy; and X is selected from the group consisting of a 2- or 3-fluorine, chlorine, bromine, iodine, thiomethyl, methyl and hydrogen.

20. The method of claim 19 wherein R is chlorine and $R_1$, W and X are hydrogen.

21. The method of claim 19 wherein R is methoxy and $R_1$, W and X are hydrogen.

22. The method of claim 19 wherein R is nitro and $R_1$, W and X are hydrogen.

23. The method of claim 19 wherein R is iodine and $R_1$, W and X are hydrogen.

24. The method of claim 19 wherein R is methyl and $R_1$, W and X are hydrogen.

25. The method of claim 19 wherein R is cyano and $R_1$, W and X are hydrogen.

26. The method of claim 19 wherein R is bromine and $R_1$, W and X are hydrogen.

27. The method of claim 19 wherein R is fluorine and $R_1$, W and X are hydrogen.

28. The method of claim 19 wherein R is trifluoromethyl, and $R_1$, W and X are hydrogen.

29. The method of claim 19 wherein R is chlorine, $R_1$ and W are hydrogen and X is 3-chlorine.

30. The method of claim 19 wherein R, $R_1$, W and X ae hydrogen.

31. The method of claim 19 wherein R is —NH$_2$ and $R_1$, W and X are hydrogen.

32. The method of claim 19 wherein R is chlorine, $R_1$ is methyl, W and X are hydrogen.

33. The method of claim 19 wherein R is fluorine, $R_1$ is methyl, W is hydrogen and X is chlorine.

34. The method of claim 19 wherein R is iodine, $R_1$ is methyl and W and X are hydrogen.

35. The method of claim 19 wherein R is hydrogen, $R_1$ is allyl and W and X are hydrogen.

* * * * *